US006286248B1

United States Patent
Bryant et al.

(10) Patent No.: US 6,286,248 B1
(45) Date of Patent: Sep. 11, 2001

(54) ROPE-LIKE FUMIGANT

(75) Inventors: Harry E. Bryant; Donald W. Hildebrandt; Douglas P. Gundlach, all of Racine, WI (US)

(73) Assignee: S. C. Johnson & Son, Inc., Racine, WI (US)

(*) Notice: Subject to any disclaimer, the term of this patent is extended or adjusted under 35 U.S.C. 154(b) by 0 days.

(21) Appl. No.: 09/461,535

(22) Filed: Dec. 15, 1999

(51) Int. Cl.$^7$ ................................................. A01M 13/00
(52) U.S. Cl. ................................................................ 43/125
(58) Field of Search ........................... 424/40; 43/125; 119/710; 431/291, 288, 325; 149/2

(56) References Cited

U.S. PATENT DOCUMENTS

| | | |
|---|---|---|
| 593,990 | 11/1897 | Deming . |
| 1,974,037 * | 9/1934 | Atkins .................................. 431/325 |
| 2,189,412 * | 2/1940 | Arnone ................................. 431/325 |
| 2,224,622 | 12/1940 | Waples . |
| 2,279,354 * | 4/1942 | Walters ................................ 431/325 |
| 2,700,011 | 1/1955 | Taylor . |
| 2,765,579 | 10/1956 | Gordon . |
| 2,818,718 * | 1/1958 | Roberts ............................... 431/291 |
| 2,829,511 * | 4/1958 | Oesterle et al. ..................... 431/325 |
| 2,912,742 * | 11/1959 | Choate ................................. 112/400 |
| 2,918,750 | 12/1959 | Blatt . |
| 3,293,888 * | 12/1966 | Fry ...................................... 431/314 |
| 3,462,235 * | 8/1969 | Summers ............................. 431/289 |
| 3,754,861 * | 8/1973 | Sadahiro ............................. 422/126 |
| 4,099,916 * | 7/1978 | Gardner et al. ..................... 422/126 |
| 4,515,768 | 5/1985 | Hennart et al. . |
| 4,600,146 | 7/1986 | Ohno . |
| 4,839,144 | 6/1989 | Martin . |
| 4,878,832 * | 11/1989 | Lynch .................................. 431/120 |
| 4,938,144 | 7/1990 | Demarest . |
| 4,959,925 | 10/1990 | Nelson et al. . |
| 4,964,427 * | 10/1990 | Case et al. .......................... 131/365 |
| 5,256,059 * | 10/1993 | Knippenberg ....................... 431/289 |
| 5,447,713 | 9/1995 | Elsner et al. . |
| 5,477,815 * | 12/1995 | O'Rourke ............................ 119/710 |
| 5,501,750 * | 3/1996 | Smith et al. .............................. 149/2 |
| 5,657,574 | 8/1997 | Kandathil et al. . |
| 5,690,484 * | 11/1997 | Leonard et al. .................... 431/291 |
| 5,807,539 | 9/1998 | Tsukii et al. . |
| 5,879,694 | 3/1999 | Morrison et al. . |
| 5,932,204 | 8/1999 | Joshi . |

OTHER PUBLICATIONS

V. Sharma et al., Insecticide Impregnated Ropes As Mosquito Repellent; Indian Journal of Malariology; vol. 26; 1989; pp. 179–185.*

M. Ansari et al., Field Trial Of Esbiothrin–Impregnated Rope In Ramgarh Village, Dadri PHC, District Ghaziaad (U.P.); Indian Journal Of Malariology; vol. 31, 1994; pp. 57–64.

M. Ansari et al., Esbiothrin–Impregnated Ropes As Mosquito Repellent; Indian Journal Of Malariology; vol. 29; 1992; pp. 203–210.

PIC Corporation advertisement entitled "Mosquito Repellent Sticks" undated, admitted prior art.

* cited by examiner

*Primary Examiner*—Charles T. Jordan
*Assistant Examiner*—J Lofdahl

(57) ABSTRACT

Disclosed are rope-like fumigants. The rope-like fumigants are sufficiently sturdy thick, or tightly twisted or braided that they can be generally vertically positioned without drooping at their top, even though they are considerably elongated. The rope-like fumigants are loaded with an insecticide, fragrance, or the like, and lit from the top. Very low cost materials such as jute, hemp, or the like form the base material for the fumigant. A holder is disclosed which retains the rope-like fumigant in a vertical position from its lower portion, while reducing the incidence of the fumigant's prematurely extinguishing. A method of controlling insects by use of the fumigant is also disclosed.

15 Claims, 2 Drawing Sheets

ROPE-LIKE FUMIGANT

CROSS REFERENCES TO RELATED APPLICATIONS

Not applicable.

STATEMENT REGARDING FEDERALLY SPONSORED RESEARCH

Not applicable.

BACKGROUND OF THE INVENTION

The present invention relates to vertically disposed, rope-like structures that are ignitable from their top to dispense desired volatile materials, including, by way of example only, insect control actives such as insect repellents.

The fact that certain combustible materials can be ignited and will then disperse an active ingredient as they continue to smolder is well known. Incense sticks and mosquito coils are examples of products made from such materials. See e.g. U.S. Pat. Nos. 4,959,925 and 5,657,574. The disclosure of these publications and of all other publications referred to herein are incorporated by reference as if fully set forth herein.

The term "fumigant" herein means a burnable material that releases a volatile ingredient as the material burns, and preferably as it slowly smolders. A "volatile material" or "volatile ingredient," in that context, means any material that can be released by a burning fumigant including, by way of example only, fragrances, disinfectants, and insect control actives. The term "active" refers to a volatile material to be released in order to achieve the desired effect of the fumigant. For a fumigant intended to repel mosquitoes, for example, an insect repellant would be an "active." An "insect control active" is an active that repels, kills, or desirably modifies the behavior of insects. "Insects" herein means actual insects, as well as other small animals commonly controlled in conjunction with insects, such as spiders and the like.

While conventional fumigants in the form of mosquito coils or repellent sticks are fairly inexpensive, they are often used in large quantity (e.g. thirty or so a month may be needed to control mosquitoes on an overnight basis). Further, these coils are most often used in countries having average annual income levels that are very low. In order to make such products more widely available, their cost must be reduced still further. This is particularly important in controlling the spread of malaria and certain other insect-borne diseases.

There have been attempts to reduce the cost of mosquito protection by burning widely available, very inexpensive, smoke-producing materials that are used without any insecticide. However, efforts to control mosquitoes by burning materials of this type, such as by burning cow dung, are not very effective and can have other undesirable characteristics, such as excessive odor.

Academic researchers in India have proposed the use of jute rope that has been impregnated with a mosquito repellant as a fumigant. This approach uses a relatively limp impregnated rope suspended from a hanger, which is lit on its lower end and permitted to smolder overnight. See M. Ansari et al., 31 Indian J. Malariology 57–64 (1994); M. Ansari et al., 29 Indian J. Malariology 203–210 (1992); and V. Sharma et al., 26 Indian J. Malariology 179–185 (1989).

Unfortunately, this technique produces inconsistent results as burning rates can not be precisely controlled and, especially, can be too rapid. Also, there is some fire risk if the characteristics of the rope are not carefully controlled. For example, fire can flash up the rope, contacting structures from which the rope has been hung. Metal mesh fire guards have been shown to attempt to control this risk. Further, a portion of the rope is sometimes wasted near its upper end, as contact with the suspension device snuffs the rope.

Wax candles, having conventional fiber wicks surrounded by wax, are of course also well known. They are sometimes supported in a hollow core of a corkscrew-like wire, positioned on a flat surface. Some such candles have insect repellent (such as citronella) incorporated in the wax. However, such designs require the use of relatively expensive candle wax.

Thus, there is still a need for improved fumigants, particularly those that can dispense insecticide or insect repellent at extremely low cost.

SUMMARY OF THE INVENTION

In one aspect, the invention provides a burnable fumigant. It has an elongated, preferably twisted or braided strand or otherwise formed rope or rope-like structure (preferably of at least 5 mm in diameter) which is sufficiently rigid that, when supported from its lower half, it maintains its upper half in a position sufficiently upright that the uppermost end of the rope-like structure remains at least level with or, preferably, above the remainder of the rope-like structure, even without an external support contacting its upper half. It is preferred that the upper half, when so held, droop no more than about 80 degrees from the vertical and, more preferred for easy holding and use, no more than 45 degrees. Ideally, the upper half should remain substantially vertical when so held. All such orientations will sometimes be referred to herein as being "functionally vertical." Preferably the rope-like structure remains functionally vertically disposed even when supported over no more than its lower third, better over no more than its lower fourth, and ideally over no more than its lower eighth.

While the rope-like structure can include braided or twisted strands, it can also be made from strands formed into a rope-like structure by being compacted, felted, or similarly processed. The rope-like structure can be made of a very inexpensive material such as jute or other fibrous plant materials.

There is an active on the surface of, impregnated in, or otherwise borne by the rope-like structure. The active preferably is an insect control ingredient, a fragrance, or a combination of the two. In especially preferred forms, the active includes an insecticide or an insect repellent. Two such actives are esbiothrin (d-trans chrysanthemate of d-allethrolone) and Pynamin Forte® (d-cis-trans-chrysanthemate of dl-allethrolone), both available from AgrEvo Environmental Health, Inc. and Sumitomo, respectively.

In one embodiment, a strand or other longitudinally extending first portion of the rope-like structure has either no active or only selected actives. Another, co-extending, second portion of the rope-like structure does have one or more actives not present in the first portion and, preferably, also is colored, preferably with a dye, so that the second portion is visually distinguishable from the first portion. This provides a quality control feature to insure inclusion of a specifically treated strand in the final product, minimizes the amount of active needed for any given height and thickness of the structure, may also provide perceived value in the mind of the consumer, and can be used to visually distinguish among different actives or active concentrations in otherwise similar products. Thus, by way of example only, a product having a higher concentration of active for use in extreme conditions can be distinguished at a glance from a low active concentration product.

The rope-like structure preferably is literally a rope between 5 mm and 15 mm in diameter. With this diameter, tightly wound jute rope, held vertically from the bottom, typically can extend upwardly as much as 30 cm and remain functionally vertical. A length of rope held generally vertically from the bottom for burning from its upper end will sometimes be called a "rope candle" herein. The rope candle preferably is held up in a coil holder that supports it only from its lower half (preferably only from its lower third, more preferably from its lower fourth, or, ideally, its lower eighth). This reduces the likelihood that contact between the holder and smoldering rope will extinguish the rope prematurely.

Another form of the invention provides a method of controlling insects. One positions the above fumigant such that it is functionally and preferably essentially vertically disposed and ignites an upper end of the fumigant. Preferably, the upper end is treated with an igniter material such as sodium nitrate.

A wide variety of insect control actives are suitable for use with the present invention. Pyrethrum or pyrethroid type materials of the type that have been successfully used in mosquito coils are preferred. Especially preferred insect control actives (from the standpoint of expense and activity vis a vis mosquitoes) are pyrethrum, esbiothrin, Pynamin Forte, resmethrin, bioallethrin, allethrin, and mixtures thereof. Other insect control ingredients can also be used, such as the repellents citronella, lemon grass oil, lavender oil, cinnamon oil, neem oil, clove oil, sandlewood oil, and geraniol, and insect growth regulators such as hydroprene.

A variety of known fragrances (e.g. those typically incorporated in incense sticks) can be used instead of or in addition to the insect control ingredient. A wide variety of volatile fragrances are well known to those skilled in the art.

Because the rope candle is burnt from its upper end, the burning process proceeds much more uniformly and slowly than if it were ignited from its lower end, and with reduced risk of fire. Also, because the rope structure can be twisted or braided firmly, the fumigant is sufficiently vertically rigid that it does not so droop as to interfere with its functioning, at least over useful lengths up to about 30 cm. Compared to the length of the rope candle, only a relatively short holder is sufficient to hold the rope candle for use. Preferably the holder is made in the shape of a coil and is made of very thin wire. This insures only minimal contact at any height between the supporting coil and the burning portion of the rope. Consequently, the risk of the rope candle being extinguished by its holder is markedly reduced.

The rope can be made from any of a wide variety of naturally occurring stranded plant materials. By way of example, only, while preferred ropes can be made from jute, other stranded structures can be made from portions of hemp, cotton, maize straw, rice straw, coir fiber, sisal, henequen fiber, and abaca fiber.

These and still other advantages of the present invention will be apparent from the description of the preferred embodiments which follows. It should be appreciated that the following embodiments are merely the preferred embodiments. Thus, the claims should be looked to in order to judge the full scope of the invention.

DETAILED DESCRIPTION OF THE PREFERRED EMBODIMENTS

Figure 1:
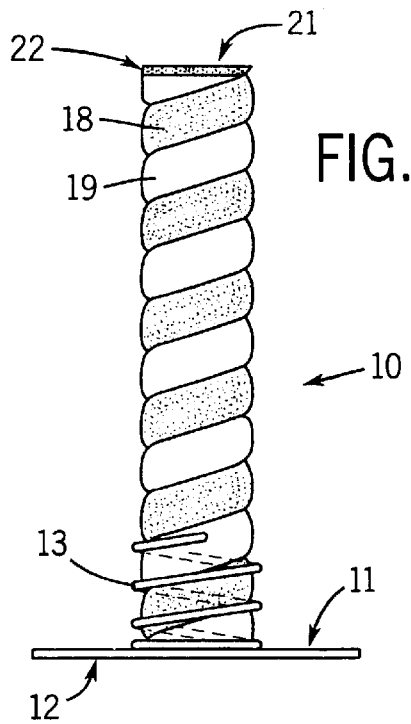
FIG. 1 is a front view of a rope structure of the present invention, supported in a holder.
Figure 2:
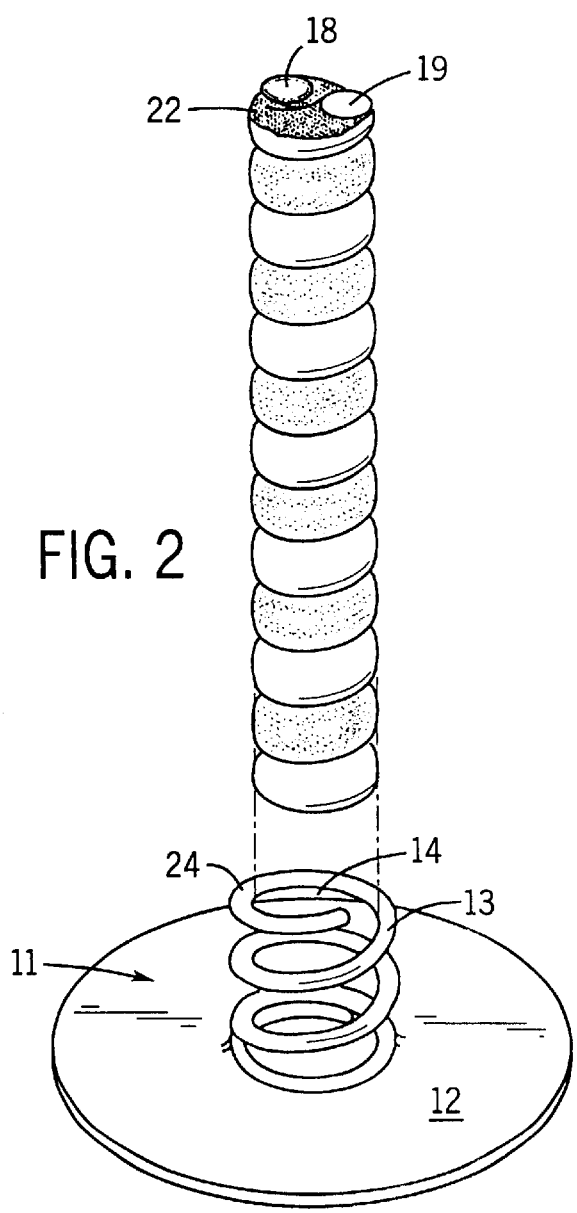
FIG. 2 is an exploded perspective view of the FIG. 1 assembly.
Figure 3:
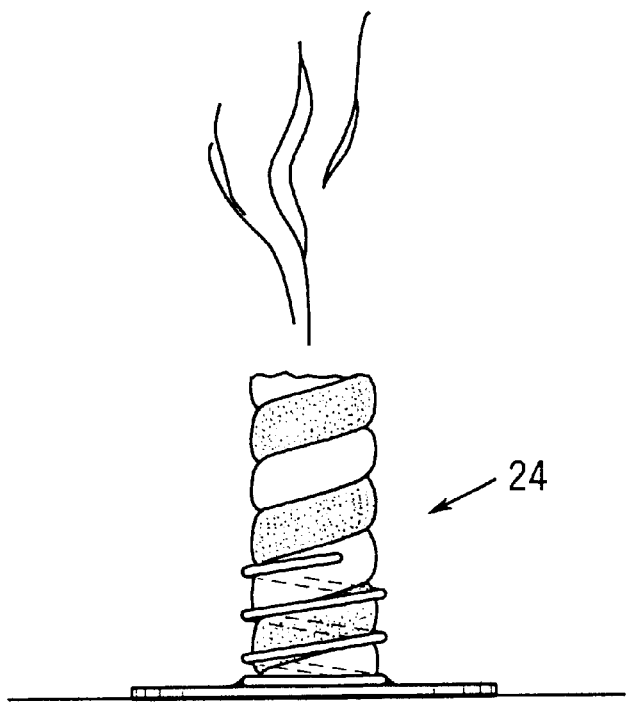
FIG. 3 shows the FIG. 1 rope structure during a smoldering process.

FIG. 1 depicts a rope structure, generally 10. It is positioned in a holder 11 which is made from a metal disk 12 to which is welded a metal wire coil 13. Alternatively, the coil can be extracted out of the disk center after the center has been appropriately cut. There is a central hollow area or core 14 extending lengthwise through the coil and having a diameter sufficient to receive the bottom of rope structure 10.

Rope structure 10 may be formed from braided or twisted strands or from strands formed into a rope-like structure by being compacted or felted. For example. FIG. 1 shows two strands 18, 19 being twisted together, but three strand or braided ropes can also be used. In the FIG. 1 embodiment, strand 19 is not impregnated with active while strand 18 is both impregnated with active and colored with a dye, prior to the strands being twisted into a rope.

After the twisting, segments of the rope (typically between 8 cm to 10 cm long) can be cut. Preferably the top 21 of the rope structure 10 is dipped in an igniter solution (e.g. a sodium nitrate solution) to provide an igniter section 22.

After insertion of the rope structure 10 in the core 14, the wire holder 11 extends no more than a third of the way up the rope structure 10. Nevertheless, the rope structure 10 is sufficiently tightly wound and sufficiently wide so as to prevent its upper portion from drooping to an extent that interferes with the use of the invention. Drooping beyond 80 degrees from the vertical so interferes, and preferably the rope structure droops no more than 45 degrees from the vertical.

The rope structure 10 can then be lit from its top. Because the wire around the coil 13 is very thin (e.g. preferably not more than about 2 mm diameter), and because of the helical nature 24 of the preferred coil, at any vertical height only a small portion of the wire contacts the rope structure 10 and from only one side at any given height. As a result, the rope structure 10 will be able to burn almost entirely down to the bottom without being extinguished, whether by being snuffed out or by being extinguished by excessive conductive heat loss via the wire. Thus, there is less waste.

Figure 4:
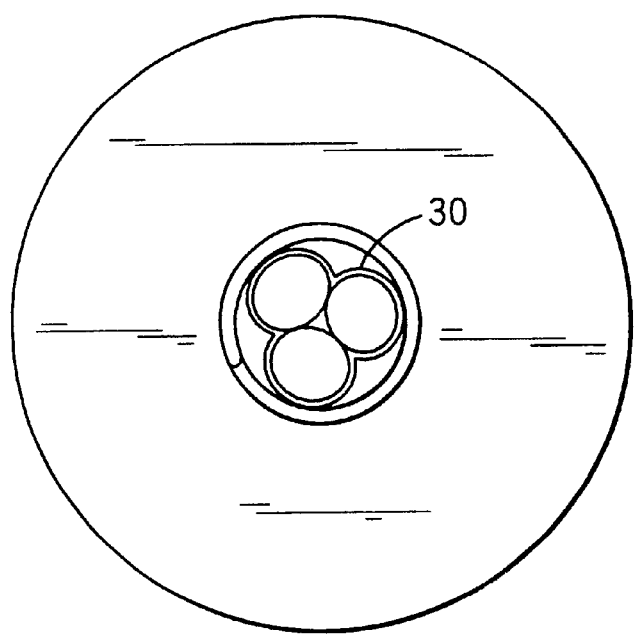
FIG. 4 depicts a top view of a second embodiment of a rope structure, positioned in the FIG. 1 holder.

In the alternative embodiment shown in FIG. 4, the rope structure 30 is braided. Preferably the braided structure, as a whole and after the braiding, is dipped into the active solution such that the active coats on the surface of the structure or even soaks into it. However, it is also possible to pre-treat a component strand that then is incorporated in the otherwise untreated rope in the braiding process.

The impregnating/coating solution contains an organic solvent, such as isopropyl alcohol or a hydrocarbon such as Isopar M (from Exxon Chemical Co.). A dipping protocol is used that results in the rope structure holding from 1 to 3 mg of active per that length of the rope structure that will burn in one hour.

When a dye is used in the dipping solution, it is preferably in the percent weight range of 0.001% to 0.1%. One preferred dye is the common fabric dye Malichite green.

However, any suitable dye that does not produce detrimental fumes may be used.

As indicated above, sodium nitrate is a preferred igniter material. It is applied in a 1 to 10% solution dissolved in water, most conveniently by merely dipping the end of the rope structure into the solution and then allowing it to dry.

The burning rate of the rope can be adjusted by adding any convenient combustion rate-modifying material to the dipping solution. For example, when it is desired to retard the burning rate, boric acid (e.g. 0.2%) can be added to the dipping solution. This may be desirable where the type of plant material used has a tendency to burn too quickly.

EXAMPLE

A jute rope twisted from three primary strands was dipped in an isopropyl alcohol solution of Pynamin Forte at a concentration such that 8.75 mg of Pynamin Forte was deposited for each 15.4 cm (6 inches) of rope. After drying, the top end was dipped in an igniter made from a 1% aqueous solution of sodium nitrate.

After the igniter had dried, the rope structure was then mounted in the FIG. 1 holder and lit at its upper end at around sunset in selected user test sites. Reports received indicated that the ropes provided mosquito protection comparable to that provided by conventional mosquito coils.

Note that the rope may be made having widths and lengths either wider and less tall or narrower and taller than the embodiments depicted in the drawings. Further, more than one strand may be dyed in more than one color for various aesthetic, indicia, or trademark purposes. Also, various fragrances may replace and/or be used in addition to, the insect control active.

Thus, the claims should be looked to in order to understand the full scope of the invention.

Industrial Applicability

Fumigants are disclosed that control mosquitoes at very low cost. Methods of using such fumigants are also disclosed.

What is claimed is:

1. A burnable fumigant, comprising:
   a. an elongated, rope-like structure that has upper and lower ends, is supported over no more than its lower half, and is sufficiently rigid that it remains in a functionally vertical position when placed upright and supported over no more than its lower half; and
   b. a volatilizable active borne by the rope-like structure and capable of being released therefrom by the heat generated by allowing the rope-like structure to burn.

2. The fumigant of claim 1, wherein the rope-like structure is supported over no more than its lower third and will remain in a functionally vertical position when supported over no more than its lower third.

3. The fumigant of claim 1, wherein the rope-like structure is supported over no more than its lower fourth and will remain in a functionally vertical position when supported over no more than its lower fourth.

4. The fumigant of claim 1, wherein the rope-like structure is supported over no more than its lower eighth and will remain in a functionally vertical position when supported over no more than its lower eighth.

5. The fumigant of claim 1, wherein the volatilizable active is selected from the group consisting of insect repellants and insecticides.

6. The fumigant of claim 1, wherein the rope-like structure is made from natural plant material.

7. The fumigant of claim 1, wherein the rope-like structure includes a first portion that bears a volatilizable active, and a second portion co-extending along side the first that bears either no volatilizable active or bears a volatilizable active different from the volatilizable active borne by the first portion.

8. The fumigant of claim 7, wherein the first and second portions are both visible along an external side of the fumigant and are visually distinguishable from each other.

9. The fumigant of claim 8, wherein one of the first and second portions is marked with a dye.

10. The fumigant of claim 1, further comprising a wire coil holder wrapped around a lower outer periphery of the fumigant in which the rope-like structure is held.

11. The fumigant of claim 1, wherein the fumigant also contains a combustion rate-modifying material.

12. The fumigant of claim 11, wherein the fumigant also contains boric acid.

13. The fumigant of claim 1, wherein the rope-like structure is treated with sodium nitrate at its upper end.

14. A method of controlling insects comprising the steps of:
   a. providing a burnable fumigant that includes:
      i. an elongated, rope-like structure that has upper and lower ends, is supported over no more than its lower half, and is sufficiently rigid that it remains in a functionally vertical position when placed upright and supported over no more than its lower half; and
      ii. a volatilizable insect control active borne by the rope-like structure and capable of being released therefrom by the heat generated by allowing the rope-like structure to burn; and
   b. igniting the upper end of the rope-like structure.

15. The method of claim 14, wherein the volatilizable insect control active is selected from the group consisting of insect repellents and insecticides.

* * * * *

UNITED STATES PATENT AND TRADEMARK OFFICE
CERTIFICATE OF CORRECTION

PATENT NO.    : 6,286,248 B1
DATED         : September 11, 2001
INVENTOR(S)   : Harry E. Bryant, Donald W. Hildebrandt and Douglas P. Gundlach It is certified that error appears in the above-identified patent and that said Letters Patent is hereby corrected as shown below:

Column 5,
Line 43, in claim 1, revise the claim as follows:
-- 1.   A burnable fumigant, comprising:
   a.   an elongated, rope-like structure that has upper and lower ends, is supported over no more than its lower half, and is sufficiently rigid that it remains in a functionally vertical position when placed upright and supported over no more than its lower half; and
   b.   A volatilizable active, selected from the group consisting of fragances, disinfectants, and insect control actives, borne by the rope-like structure and capable of being released therefrom by the heat generated by allowing the rope-like structure to burn;
       wherein the rope-like structure is selected from the group consisting of multiple tightly twisted strands and multiple tightly braided strands. --

Column 6,
Line 48, change to final period to semi-colon, and add thereafter:
       -- wherein the rope-like structure is selected from the group consisting of multiple tightly twisted strands and multiple tightly branded strands. --

Signed and Sealed this

First Day of October, 2002

*Attest:*

*Attesting Officer*

JAMES E. ROGAN
*Director of the United States Patent and Trademark Office*